US006551798B2

(12) United States Patent
Gao et al.

(10) Patent No.: US 6,551,798 B2
(45) Date of Patent: Apr. 22, 2003

(54) METHOD FOR USING A YEAST ALPHA-AMYLASE PROMOTER

(75) Inventors: Johnway Gao, Richland, WA (US); Rodney S. Skeen, Pendleton, OR (US); Brian S. Hooker, Kennewick, WA (US); Daniel B. Anderson, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/921,942

(22) Filed: Aug. 2, 2001

(65) Prior Publication Data

US 2002/0127724 A1 Sep. 12, 2002

Related U.S. Application Data (63) Continuation-in-part of application No. 09/632,313, filed on Aug. 4, 2000.

(51) Int. Cl.[7] ........................... C12N 15/63; C12N 15/82
(52) U.S. Cl. ...................... 435/69.1; 435/419; 435/468; 536/24.1; 800/278
(58) Field of Search .............................. 435/69.1, 71.1, 435/483, 471, 468; 536/24.1; 800/278

(56) References Cited

U.S. PATENT DOCUMENTS 4,676,986 A 6/1987 Sills et al.
5,100,794 A 3/1992 Strasser et al.

FOREIGN PATENT DOCUMENTS

EP 0257115 A1 2/1988

OTHER PUBLICATIONS

Shin et al., "Construction of a Secretory Expression Vector Producing an α–Amylase of Yeast, Schwanniomyces occidentalis in Saccharomyces", J. Microbiol. Biotechnol., 1998, 8(6), 625–630.
Wang et al., "Cloning of α–amylase gene from Schwanniomyces occidentalis and expression in Saccharomyces cerevisiae" Science in China (Series C), vol. 41 No. 6, Dec. 1998.
Sills et al., "Isolation and Characterization of the Amylotic System of Schwanniomyces castellii", J. Inst. Brew., Sep.–Oct., 1984, vol. 90, pp. 311–314.
AM Sills et al., "Production of Amylolytic Enzymes by Several Yeast Species", pp. 313–316. 1982. J. Inst. Brew., vol. 88.
T Hongpattarakere et al., "Optimization of Single–Cell–Protein Production From Cassava Starch Using Schwanniomyces castellii", pp. 607–609. 1995. World Journal of Microbiology & Biotechnology. vol. 11.

SA Lemmel et al., "Kinetics of Growth and Amylast Production of Saccharomycopsis fibuligera on Potato Processing Wastewater", p. 387–393. 1980. Applied and Environmental Microbiology, vol. 39.
K Kim et al., "High–Efficiency, One–Step Starch Utilization by Transformed Saccharomyces Cells Which Secrete Both Yeast Glucoamylase and Mouse a–Amylase", p. 966–971. 1988. Applied and Environmental Microbiology, vol. 54.
C Laluce et al., "New Amylolytic Yeast Strains for Starch and Dextrin Fermentation", p. 2447–2451. 1988. Applied and Environmental Microbiology, vol. 54.
Piper, P. "Isolation of Yeast DNA" in Yeast Protocols, p. 103–107. 1996. Methods in Molecular Biology, 53, Humana Press, Inc., Totowa.
K Pirselova et al., "Fermentation of Starch to Ethanol by a Co–Culture of Saccharomycopsis fibuligera and Saccharomyces cerevisiae", p. 338–341. 1993. World Journal of Microbiology and Biotechnology, vol. 9.
YW Ryu et al., Direct Alcohol Fermentation of Starch by a Derepressed Mutant of Schwanniomyces castellii, p. 107–112. 1994. Biotechnology Letters, vol. 16.
K Sreekrishna et al., "High–Level Expression, Purification, and Characterization of Recombinant Human Tumor Necrosis Factor Synthesized in the Methlotroppic Yeast Pichia Pastoris", p. 4117–4125. 1989. Biochemistry, vol. 28.
JM Cregg et al., "Recent Advances in the Expression of Foreign Genes in Pichia Patoris", p. 905–909. 1993. Bio/Technology, vol. 11.
D Porro et al., "Replacement of a Metabolic Pathway for Large–Scale Production of Lactic Acid From Engineered Yeasts", p. 4211–4215. 1999. Applied and Environmental Microbiology, vol. 65.
NWY Ho, "Successful Development of Hazard–Free, User–Friendly, Genetically Engineered Microorganisms for Effective Production of Environmentally Friendly Chemicals from Renewable Biomass", p. 77–78. 1999. Green Chemistry, 3rd Annual.
TT Wang, et al., "The Molecular Biology of Schwanniomyces occidentalis Klocker", p. 113–143. 1999. Critical Reviews in Biotechnology, vol. 19.
TM Downhanick et al., "Expression and Regulation of Gluoamylase From the Yeast Schwanniomyces castellii", p. 2360–2366. 1990. Journal of Bacteriology vol. 172.
RJ Dohmen et al., "Cloning of the Schwanniomyces occidentalis Glucoamylase Gene (GAMI) and its expression in Saccharomyces cerevisiae", p. 111–121. 1990. Gene, vol. 95.
Klein et al. A DNA fragment containing the ADE2 gene from Schwanniomyces occidentalis can be maintained as an extrachromosomal element Gene V 97. 1991. 183–189.
RA Jefferson et al., "GUS Fusions: β–Glucuronidase as a Sensitive and Versatile Gene Fusion Marker in Higher Plants", p. 3901–3907. 1987. The EMBO Journal, vol. 6.
Claros et al., Curr. Genet. 24:75–83. 1993.
Park et al., FEMS Microbiology Letters 93:17–24. 1992.
Strasser et al., Eur. J. Biochem. 184:699–706. 1989.

*Primary Examiner*—James Ketter
*Assistant Examiner*—Bronwen M. Loeb
(74) *Attorney, Agent, or Firm*—Wells St. John P.S.

(57) ABSTRACT

The present invention provides the promoter clone discovery of an alpha-amylase gene of a starch utilizing yeast strain Schwanniomyces castellii. The isolated alpha-amylase promoter is an inducible promoter, which can regulate strong gene expression in starch culture medium.

8 Claims, 7 Drawing Sheets

SCst Genomic DNA    AM Promoter → AM gene ORF

RE digested and self-ligated

Inverse PCR

AM Promoter →

```
   1    agatcttcaaataataatagatcctatgttgatataagatcaactccaccattgaccaat    60
  61    tcatttaatcagcctcaacaacctcagcaatcaatcaccgattctcctacccctcaacat   120
 121    catcaccaacattttttccaacgcaatcaattccttccaattctcaaccatccaccccg   180
 181    ttggcttcaaatgatatcaattcaagatttcaaccatttggtcaacatacccatttagct   240
 241    ggtagttttacgtcattacagcaatcaacctcaacttcgcaattagatgattttagtaat   300
 301    cctacttcaacaggtacgaatgttaatgactcaataagtaataaatttaattcattaaat   360
 361    ttatcaaataataattatgataattcctcaggaatttggggtttaaaataaacaaacctt   420
 421    ttgaaactccaacattcaactctttaatgtaatttatgattatgataaatgaatattttt   480
 481    tattcttttgaataaaaatttcgaataaaatattaataagatgacaaaaaatgaataca   540
 541    tgaatatacatatactttatttaaaaaattaatccttttgattaattgatgattttgctc   600
 601    ttccaaaaagaaagaatcccagaaaataacaagttttccaaagggattaacaaaattttt   660
 661    ttcctatttttttatcttttatcataatatagttctagttcaatacgttttccaaaaat   720
 721    gcaaagtgaaaaaaattttaaaaaaacatttcgaattacaaaaaaaagttcattaaat   780
 781    attattttattttatcctatattatttctaaacgatcttgaacaagtaacgttgttatta   840
 841    ctaccccgaaggagaaaaagaaatgattcataacatgaagtaatgctcacttaaaataa   900
 901    cactgttaatactttttaatatatattaatgtgcctctaatagattatatattattgtt   960
 961    tgttttttttgttaataaataagttgtacatccatatttgtggttaaaactttgaaaaaa  1020
1021    ttattgttgtgacgacgtcacttggatcttatgaaagtttatttcaacctcactacatac  1080
1081    aatttttttcagctgaaccaaattgttcaccaatccaaatcatatcagttctttctccct  1140
1141    attatcaaagtcaaattgtctctgcgtacatattttcaattatttaaaccttaattaacc  1200
1201    ttaaaaatatctacctccctgagactctacgaggggatagttagttcttcggaaatggta  1260
1261    cgtggcgctacctaccccttcccagtaactgtttcatcctgtaatagaaaccgcttaactt  1320
1321    gaatattttatattacgtcataatacagaactattattatgtgattacaatggtcggatt  1380
1381    tttcttgttgatatgtgttcgtgggtggtacctgagctaaatttagaaccggctatagat  1440
1441    ccgcttgtctaaagaagagataatgaagaaaacaattaaccgagcactcttattaagttt  1500
1501    ttttctattttcttttgctcctacttcaataatttatctaaattgtattgtgcgttagat  1560
1561    cagaatgtactgataacagagagtattatcatacacttgtggatttcaaaaggcggaatc  1620
1621    aaaagcatacgtagtcaaacccttggttatttgatgcaattaaggttgtagtcgttctta  1680
```

FIG. 4A

```
1681  ccgatccatcattataccccacacggtttcatggtatgtaggtgtttcaatagtgaagta 1740
1741  caatgaatgttttggtaatgctgttattgttggatcagtaattatgtttaaacaattaag 1800
1801  ttctggaaaatttattaaaattttacctacaattaagccgaaatccaatcgaaggtgccg 1860
1861  cccagctggtgtataaattactcttgaaattcaagttgaacgtcgatactctctaaagca 1920
1921  aagctgttattctacaatactaaataaaataaaagcaagacATGagatttttcaactgaag 1980
1981  gatttacaagtaaagttgtt                                         2000
```

METHOD FOR USING A YEAST ALPHA-AMYLASE PROMOTER

This application is a continuation-in-part of application Ser. No. 09/632,313 filed Aug. 4, 2000.

The U.S. Government has a paid-up license in this invention and the right in limited circumstances to require the patent owner to license others on reasonable terms as provided for by the terms of Contract DE-AC0676RLO1830 awarded by the U.S. Department of Energy.

FIELD OF THE INVENTION

The present invention relates specifically to the isolation of a yeast gene regulatory sequence (promoter), which is native to *Schwanniomyces castellii* and can regulate gene expression in a heterologous yeast host using starch as the sole carbon source. More specifically, the starch can be used as an inducing agent for the expression of native or foreign genes, which are fused to the isolated yeast promoter. The transformed host cells bearing the promoter-gene fusion can grow in culture medium containing various carbon sources, and the gene expression is induced by starch addition as a gene expression inducing-agent. The heterologous host is preferably bacteria, yeast, mold, plant cell, plant tissue, and whole plant.

DESCRIPTION OF THE RELATED ART

Natural yeast strains have been identified that can use starch as a primary growth substrate via complete or partial enzymatic hydrolysis. These yeast strains include but are not limited to *Saccharomycopsis fibuligera, Schwanniomyces castellii,* and *Saccharomyces diastaticus,* which can produce and secrete both alpha-amylase and glucoamylase to, liquefy and hydrolyze starch into glucose. A fusion yeast cell strain of *Saccharomyces diastaticus* and *Saccharomyces cerevisiae* could degrade 60% of starch present in culture media within two days. In addition, other natural Saccharomyces species can ferment starch and dextrin to ethanol, as well as improve ethanol production from starch and higher sugars.

The ability to genetically modify yeast strains has greatly advanced both protein expression engineering and metabolic engineering for the past two decades. The use of yeast for producing transgenic prokaryotic and eukaryotic heterologous proteins has the added advantage that yeast and filamentous mold are microbial eukaryotes, and they are more closely related to animal cells. Hence, yeasts possess the molecular genetic manipulation and growth characteristics of prokaryotic organisms, together with the subcellular machinery for performing eukaryotic post-translational protein modification. For example, *Pichia pastoris* is able to synthesize functional recombinant protein and its glycosylation abilities are very similar to those of animal cells, though the glycosylation in another yeast strain, *Saccharomyces cerevisiae,* is different from that of an animal. In addition, the metabolic pathway of a regular ethanol producing yeast strain can be genetically altered to accumulate large amounts of lactic acid and to increase xylose utilization rate. However, only a few yeast systems (transformation vector and promoters) are available for protein engineering and metabolic engineering, which include *Saccharomyces cerevisiae, Pichia pastoris,* among others.

Starch utilizing yeast strain, *Schwanniomyces castellii* or *Schwanniomyces occidentalis,* is one of the most important microorganisms, since it can directly use starch as its growth medium. Due to the low level of glycosylation and the ability of protein secretion, *Schwanniomyces castellii* is a promising host for heterologous protein expression. However, the molecular study of Schwanniomyces sp. is very limited. Only about 21 genes have been cloned, and very few promoter sequences have been cloned and characterized in their full length from Schwanniomyces sp. The ability to genetically manipulate Schwanniomyces sp. depends on the successfulness in developing the transformation methods and gene expression systems. To effectively direct the transcription or expression of an interested gene, strong gene regulating elements or promoters are required. These promoters can be isolated from the upstream sequences of strongly expressed gene clones.

Alpha-amylase, a 56-kDa protein, is one of the highly expressed clones in *Schwanniomyces castellii,* and different carbohydrates such as starch regulate its expression. The expression level of alpha-amylase can be increased about 100 times when the glucose is depleted in the culture medium. The gene regulatory element (promoter) of the alpha-amylase gene would be a useful genetic element to be used for the regulation of foreign gene expression. However, the full alpha-amylase promoter of *Schwanniomyces castellii* has never been sequenced and characterized. To genetically manipulate Schwanniomyces sp, either for the purpose of metabolic pathway modification, conferring necessary traits such as chemical production, or producing biocatalyst of interest, high levels of mRNA expression are always desirable. Therefore, there is a need to isolate strong promoter sequences of Schwanniomyces sp. and characterize its function.

The following references disclose technical information useful in this art:

Sills A M, Stewart G G. 1982. Production of amylolytic enzymes by several yeast species. *J. Inst. Brew.* 88: 313–316.

Hongpattarakere T, H-Kittikun A. 1995. Optimization of single-cell-protein production from cassava starch using *Schwanniomyces castellii J. Microbiol. Biotechnol.* 11: 607–609.

Lemmel S A, Heimsch R C, Korus R A. 1980. Kinetics of growth and amylase production of *Saccharomycopsis fibuligera* on potato processing. *Appl. Environ. Microbiol.* 39: 387–393.

Kim K, Park C S, Mattoon J R. 1988. High-efficiency one-step starch utilization by transformed Saccharomyces cells which secrete both yeast glucoamylase and mouse alpha amylase. *Appl. Environ. Microbiol.* 54: 966–971.

Laluce C, Bertolini M C, Ernandes J R, Martini A V, Martini A. 1988. New amylolytic yeast strains for starch and dextrin fermentation. *Appl. Environ. Microbiol.* 54: 2447–2451.

Pirselova K, Smogrovicova D. Balaz S. 1993. Fermentation of starch to ethanol by a co-culture of *Saccharomycopsis fibuligera* and *Saccharomyces cerevisiae. World J. Microbiol. Biotechnol.* 9: 338–341.

Ryu Y W, Ko S H, Byun S Y, Kim C. 1994. Direct alcohol fermentation of starch by a derepressed mutant of *Schwanniomyces castellii Biotechnol. Lett.* 16:107–112.

Sreekrishna K, Nelles L, Potenz R, Cruze J, Mazzaferro P, Fish W, Fuke M, Holden K, Phelps D, Wood P, Parker K. 1989. High-level expression, purification, and characterization of recombinant human tumor necrosis factor synthesized in the methylotrophic yeast *Pichia pastoris. Biochemistry* 28: 4117–4125.

Cregg J M, Vedvick T S, Raschke W C. 1993. Recent advances in the expression of foreign genes in *Pichia pastoris.* Biotechnol. 11: 905–910.

Porro D, Bianchi M M, Brambilla L, Menghini R, Bolzani D, Carrera V, Lievense J, Liu C L, Ranzi B M, Frontali L, Alberghina L. 1999. Replacement of a metabolic pathway for large-scale production of lactic acid from engineered yeasts. Appl. Environ. Microbiol. 65(9): 4211–4215.

Ho N W Y. 1999. Successful development of hazard-free, user-friendly genetically engineered microorganisms for effective production of environmentally friendly chemicals from renewable biomass. Proceedings of 3$^{rd}$ Annual Green Chemistry and Engineering Conference, Washington, D.C. Pp. 77–78.

Wang T T, Lee C F, Lee B H. 1999. The molecular biology of Schwanniomyces occidentalis Klocker. Critical Review in Biotechnol. 19(2): 113–143.

Jefferson R A, Kavanagh T A, Bevan M W. 1987. GUS fusions: beta-glucuronidase as a sensitive and versatile gene fusion marker in higher plants. *EMBO J.* 6 (13): 3901–3907.

Dohmen R J, Strasser A W M, Martens F B, Dahlems U M, Hollenberg C P. 1990. Cloning of the *Schwanniomyces occidentalis* glucoamylase gene (GAMI) and its expression in *Saccharomyces cerevisiae*. Gene 95: 111–121.

Strasser A, Martens F B, Dohmen J, Hollenberg C P. 1992. Amylolytic enzymes producing microorganisms, constructed by recombinant DNA technology and their use for fermentation processes. U.S. Pat. No. 5,100,794.

Claros M G, Abarca D, Fernandez-Lobato M, Jimenez A. 1993. Molecular structure of the SWA2 gene encoding an AMY1-related alph-amylase from *Schwanniomyces occidentalis*. Curr. Genet. 24: 75–83.

Piper P. 1996. Isolation of yeast DNA, Methods in Molecular Biology, 53:103 –107

SUMMARY OF THE INVENTION

The present invention provides the promoter clone discovery and isolation of alpha-amylase gene of a starch utilizing yeast strain *Schwanniomyces castellii*. The isolated alpha-amylase promoter is an inducible promoter, which can regulate higher gene expression in starch culture medium.

An object of the present invention is to provide an isolated yeast promoter, which is native to *Schwanniomyces castellii* (ATCC 26077) and located upstream of and in control of an alpha-amylase gene.

Another object of the invention is to provide an isolated yeast promoter that has a sequence of 1554 base pairs prior to the initiation codon of alpha-amylase gene.

Yet another object of the invention is to provide a strong gene promoter that allows effective direction of transcription or expression of a gene of interest.

Another object of the invention is to provide a process of expressing a gene of interest in bacterial, yeast, mold, and plant/plant cell species

DESCRIPTION OF THE PREFERRED EMBODIMENT(S)

The present invention comprises a promoter discovered in a starch utilizing yeast strain, *Schwanniomyces castellii* (ATCC 26077), which can completely hydrolyze and use starch in less than 10 hours. The novel promoter is related to an amylolytic enzyme, alpha-amylase. The isolated alpha-amylase promoter (AM) clone has a length of 2000 base pairs, within which 1554 base pairs are putatively determined as the promoter region, based on the open reading frame analysis. Within the 600-bp upstream of the alpha-amylase initiation codon, there are putatively ten CAT boxes and four TATA boxes, which play an important role in the regulatory mechanism of the AM promoter.

The present invention illustrates that when fused to a reporter gene, glucuronidase gene (gus), the AM promoter can regulate glucuronidase (GUS) expression in transformed Saccharomyces sp. The 1.0 kb AM promoter shows higher expression than the 1.5 kb AM promoter in both glucose and starch culture medium. In addition, the *S. castellii* AM promoter is an inducible promoter, which can regulate higher gene expression at the presence of a starch, while it can regulate minimal gene expression at the presence of glucose. The expression yield can be increased about ten times when induced in a starch culture medium as compared to the glucose culture medium.

Two alpha-amylase genes were previously isolated from *S. castellii*, ATCC 26076 and ATCC 26077 strains. However, both isolated genes only contain partial sequence of the alpha-amylase promoters, one of which has 549 base pairs, and the other 233 base pairs. In the present invention, the alpha-amylase promoter region isolated from *S. castellii* contains the full length promoter sequence of 1554 base pairs, which is about three and six times as long as the ones isolated by Dohmen et al. and Claros et al., respectively. Therefore, the alpha-amylase promoter presented in this invention has the full regulatory function for gene expression.

The inducibility of the present AM promoter provides an opportunity to regulate native or foreign gene expression in native or heterologous host strains with an inexpensive inducing agent, starch. Industrial fermentation/culture process can then use this cost-effective regulatory mechanism for certain types of metabolic pathway controlling and foreign protein accumulation.

For a clear and concise understanding of the specification and claims, including the scope given to such terms, the following definitions are provided:

PROMOTER: The expression of a gene is directed by a promoter, which is a DNA sequence and locates in the 5' region of a gene. A yeast promoter is a promoter sequence that will direct the transcription of a gene in yeast cells.

CONSTITUTIVE PROMOTER: The rate of gene transcription under such promoter is not regulated by an inducing agent, which can be a chemical compound, or a carbohydrate.

INDUCIBLE PROMOTER: The rate of gene transcription under such promoter is regulated by an inducing agent.

PLASMID VECTOR: A DNA plasmid vector contains a replicon or an origin of replication able to autonomously replicate the plasmid DNA in the original host organism. A plasmid vector can also serve as both a cloning vector for DNA manipulation in a bacterial host and a shuttle plasmid vector for interested DNA expression in another host cell.

CLONING PLASMID VECTOR: Cloning vectors typically contain one or a small number of restriction endonuclease recognition sites at which interested DNA sequences can be inserted for DNA manipulation purposes. Cloning vectors also contain a marker gene that is suitable for use in the identification and selection of cells transformed with the cloning vector. Marker genes typically include genes that provide phleomycin resistance or ampicillin resistance.

EXAMPLE 1

PCR Cloning of Alpha-Amylase Promoter of S. castellii.

Figure 1:
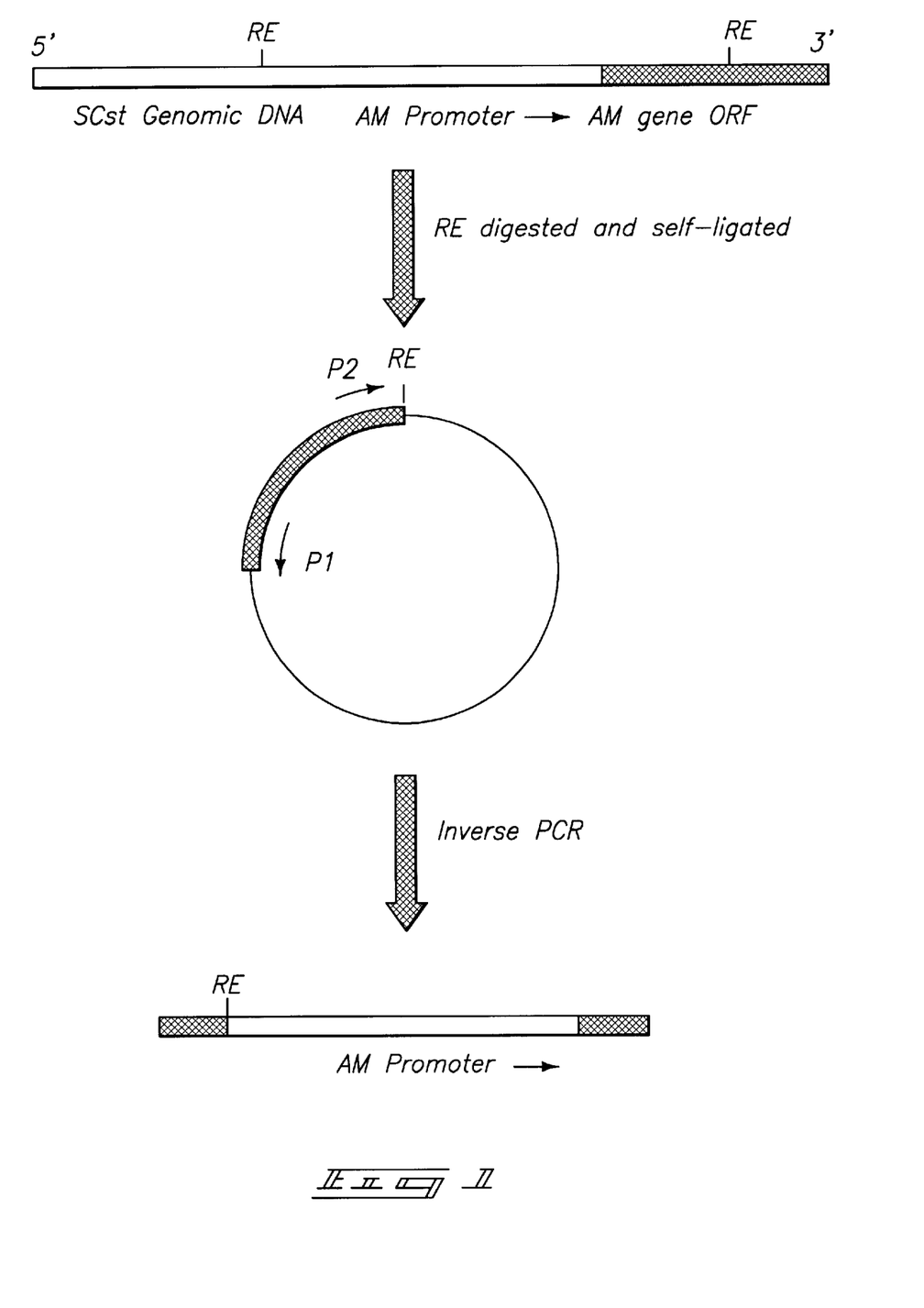
FIG. 1 is a schematic illustration depicting an inverse PCR method for promoter clone isolation.

To isolate the alpha-amylase promoter, S. castellii cells were grown overnight in a culture medium containing yeast extract 1%, peptone 2%, and glucose 2%. Cells were then harvested and genomic DNA was isolated and purified from the culture using the spheroplasting method. Inverse PCR method was used to clone out the promoter region, as shown in FIG. 1 where P1 is PCR reverse primer 1; P2 PCR forwarding primer 2; RE restriction enzyme site which can be cleaved both upstream of the alpha-amylase (AM) promoter and inside of the AM gene; SCst S. castellii PCR primers for the inverse PCR were designed based on the open reading frame of the alpha-amylase gene sequence of S. castellii. A 5' end over-hung sequence (italics) was designed to adapt restriction enzyme sites (underlined) such as Xba I and Sph I. The inverse PCR primers are listed as follows:

Reverse primer AM1-C56; SEQ ID NO:1:
5'-GAT TCT AGA AAC AAC TTT ACT TGT AAA TCC TTC AGT TGA-3'
Forwarding primer AM2-N60; SEQ ID NO:2:
5'-GAT GCA TGC ACC AAT CGA TTT ATC AAA TCG TTA-3'

Inverse PCR method was used to isolate the promoter region. In this method, the genomic DNA was first digested with different restriction enzymes, such as Bgl II, Hinc II, and Hind III, which locate within the 5' end of the alpha-amylase gene region. Upon digestion, the DNA samples were purified and self-ligated using T4 DNA ligase, and the promoter region was subsequently cloned out by the inverse PCR reaction. Table 1 shows the reverse PCR reaction matrix with different restriction enzyme conditions.

TABLE 1

Inverse PCR primer pairing conditions for each digested and ligated genomic DNA samples.

| PCR reaction No. | Restriction enzyme used before ligation | Inverse PCR primer pairing |
|---|---|---|
| 1 | Bgl II | AM1-C56; AM2-N60 |
| 2 | Hinc II | AM1-C56; AM2-N60 |
| 3 | Hind III | AM1-C56; AM2-N60 |

Figure 2:
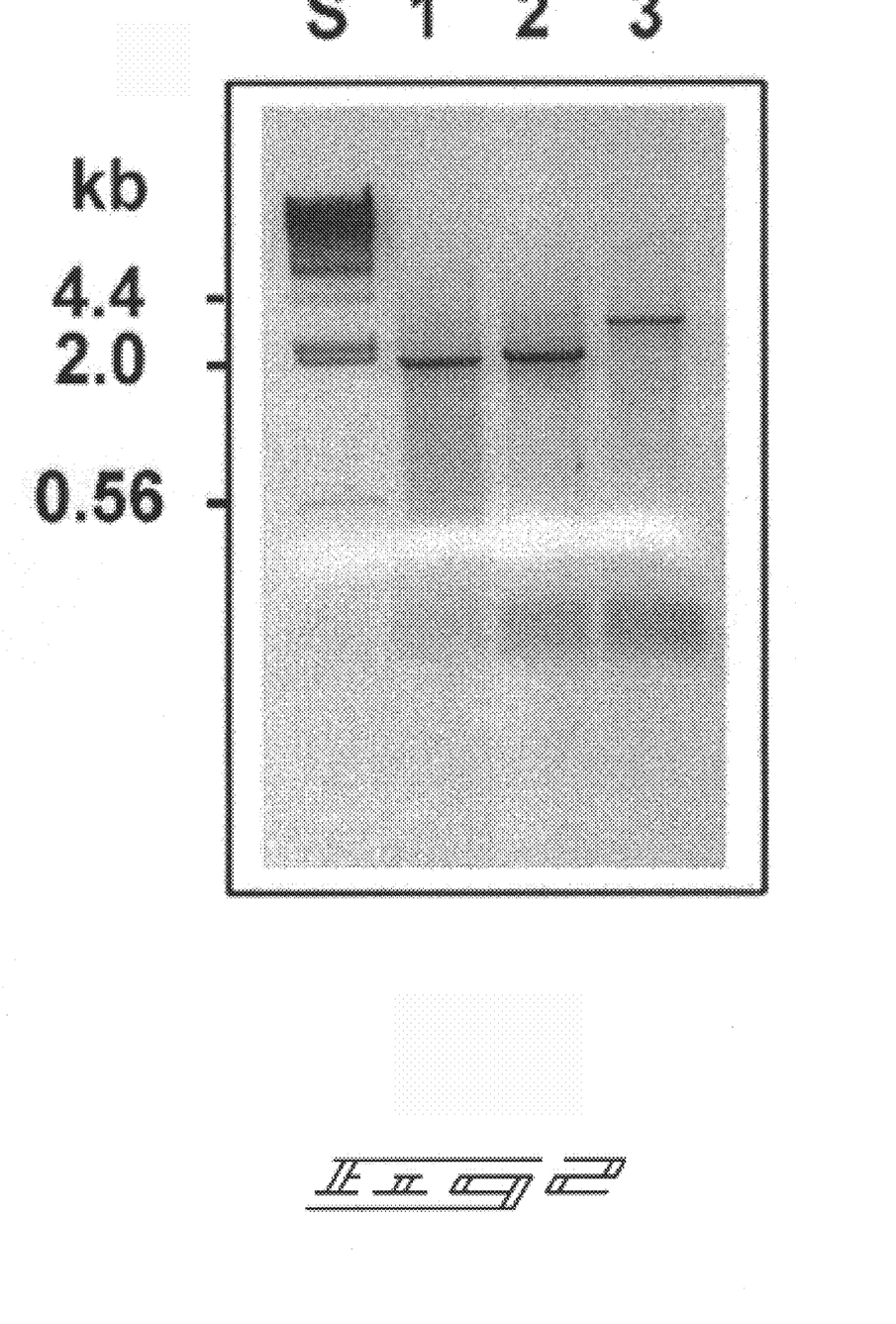
FIG. 2 is a photograph of a reverse gel image of PCR clones of *S. castellii* alpha-amylase promoter.

The inverse PCR reactions were conducted based on the primer pairing outlined in Table 1. After PCR reaction, the PCR products were separated in an agarose gel by electrophoresis. The inverse PCR results are shown in a reverse gel image in FIG. 2, where lane number is correspondent to each inverse PCR reaction in Table 1 and lane S is the Hλ DNA size marker. The isolated AM promoter clones are shown as dark bands in the gel picture. All lanes show single strong bands, which correspond to the ligated DNA samples previously cleaved by Bgl II, Hinc II, and Hind III, respectively. The sizes of the PCR clones range from about 2.0 kb to 3.0 kb.

EXAMPLE 2

Nucleotide Sequence of AM Promoter Sequence.

Figure 3:
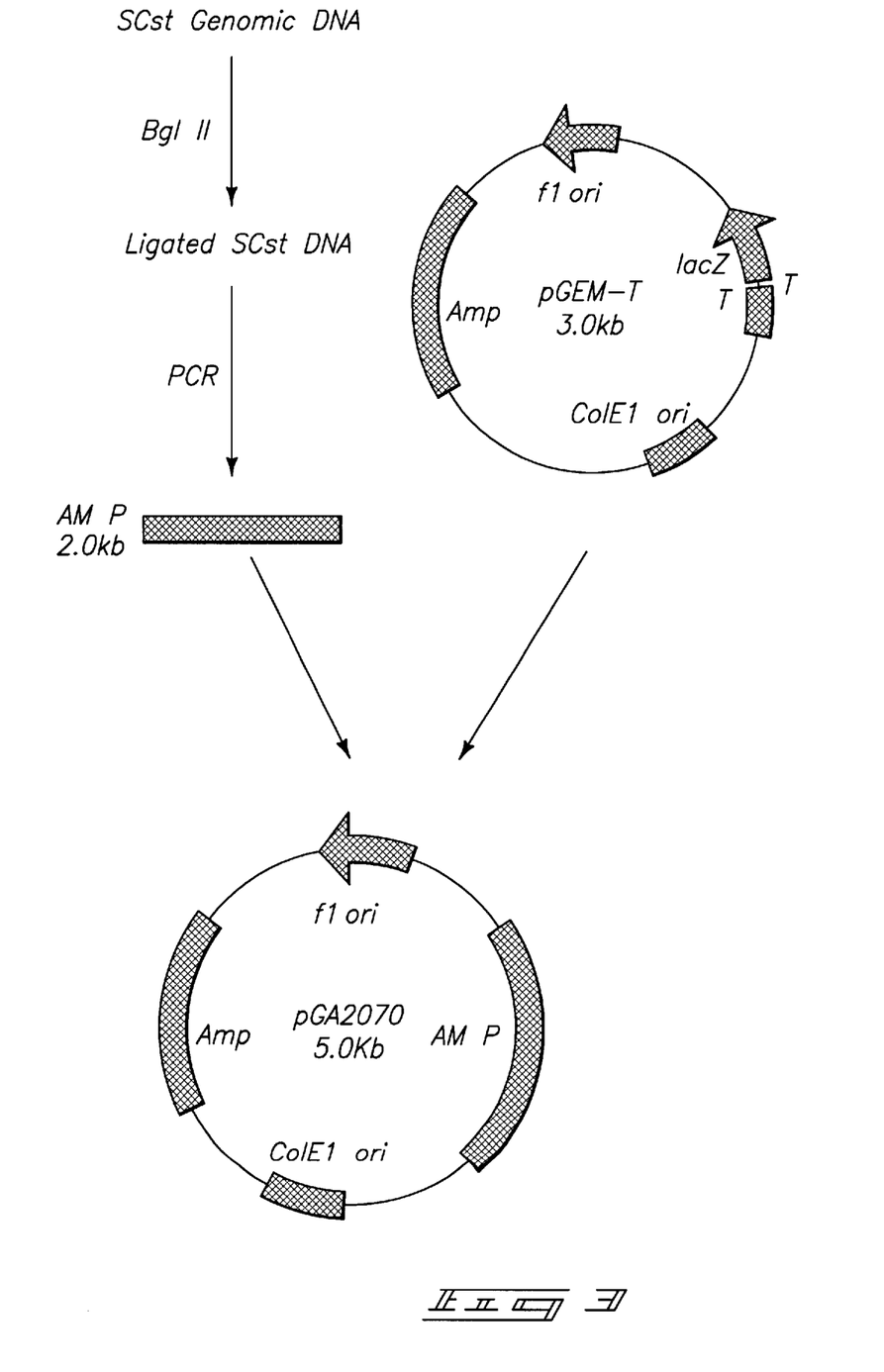
FIG. 3 is a schematic illustrating the construction of a plasmid vector pGA2070.
Figure 4A:
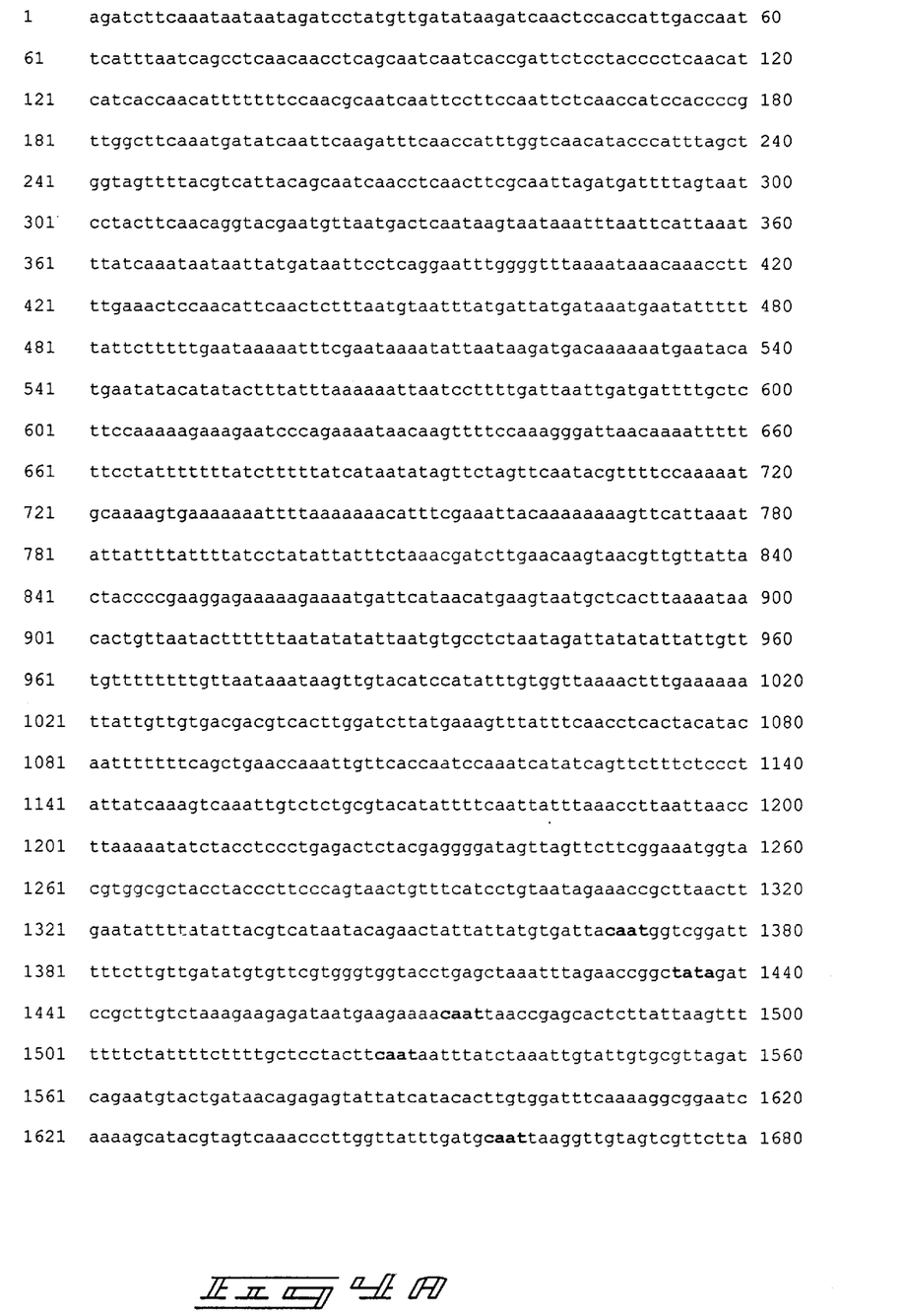
FIG. 4 is the sequence of *S. castellii* alpha-amylase promoter; SEQ ID NO:6.
Figure 4B:
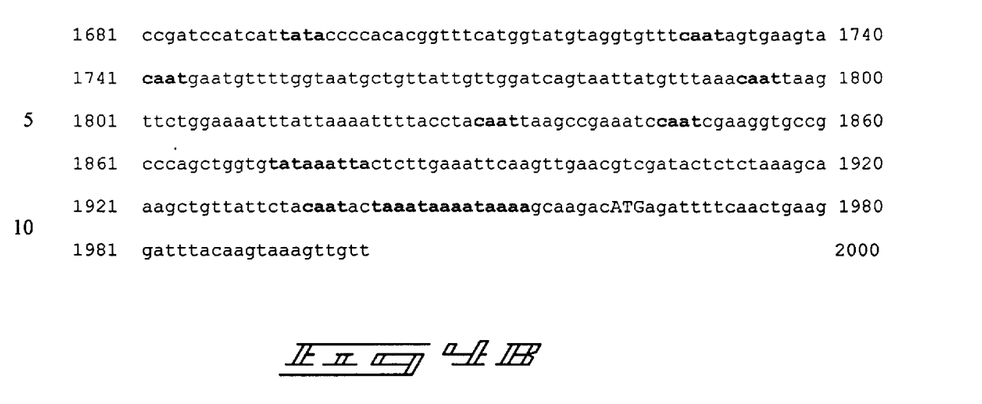

PCR product No. 1 contains sufficient length (about 2.0 kb) of the AM gene upstream sequence and the initial codon ATG of the AM gene. The AM promoter clone No. 1 was cloned into a unique cloning site containing 3' terminal thymidine (T) to both ends of a cloning plasmid vector pGEM-T (Promega, Madison, Wis.) to form pGA2070, as shown in FIG. 3, where Amp is the ampicillin resistance gene; CoE1 is the origin for plasmid replication during gene manipulation in E. coli strains; f1 ori is the phage origin. Individual colonies were picked to confirm DNA insertion. Two of the randomly picked individual clones, pGA2070-4 and pGA2070-5, were sequenced to compare the identity of those two clones. The results showed that these two clones have the same sequences. In addition, other clones from PCR products No. 3 were also sequenced, and they had the identical sequences as that of No. 1, and the sequence downstream of the initiation codon ATG is identical to the alpha-amylase gene. Therefore, the upstream of clone No. 1 contains the AM promoter region. Clone No. 1 in pGA2070-6 was chosen and completely sequenced from both ends and has a length of 2000 bps, corresponding to SEQ ID NO:6 as shown in FIG. 4. The putative TATA box and OAT box are bold and underlined. There are ten CAT boxes and four TATA boxes within 600 base pairs upstream of the initial codon. In addition, the open reading frame analysis indicates that the AM promoter sequence locates between 407 bp to 1962 bp, between which there are 1554 bps for the AM promoter, and there is no long open reading frame.

EXAMPLE 3

Vector Construction for AM Promoter Analysis.

Figure 5:
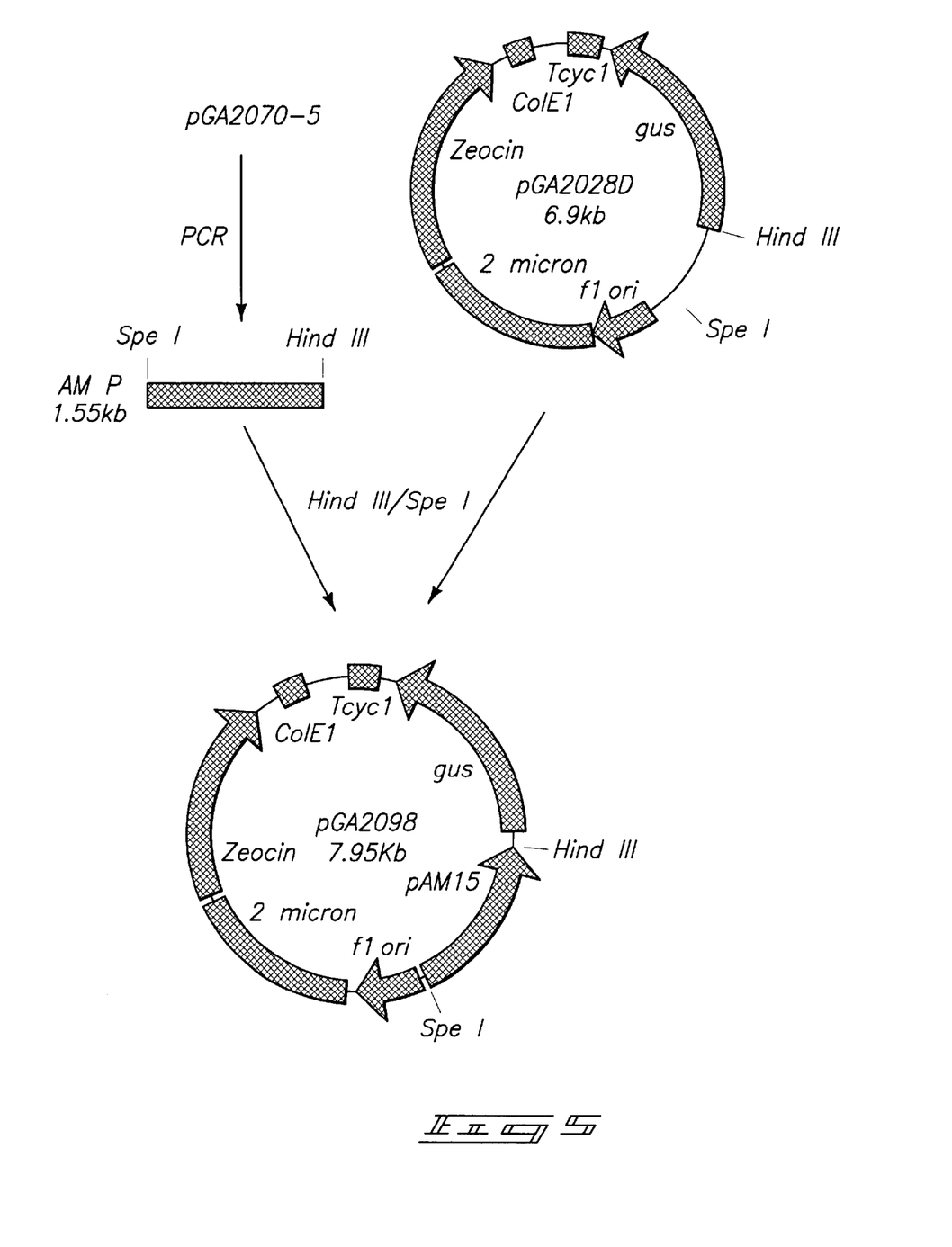
FIG. 5 is a schematic illustrating the construction of a plasmid vector pGA2098.

To test the activity of the isolated alpha-amylase (AM) promoter, a bacterial glucuronidase gene was fused to the 1.55 kb and 1.0 kb AM promoters. An episomal yeast plasmid vector pGA202BD was used, as shown in FIG. 5. The AM promoter was cloned out from pGA2070-5, forming the 1.55 kb and 1.0 kb AM promoters (AM15 and AM10). A 5' end over-hung sequence (italics) was designed to adapt restriction enzyme sites (underlined) such as Spe I at the 5' end and Hind III at the 3' end, using the following primers, respectively.

Forwarding primer AM15-N for 1.55 kb AM promoter: SEQ ID NO:3:
5'-TCT AGA ACT AGT TAT GAT AAA TGA ATA TTT TTT ATT CTT-3'
Forwarding primer AM10-N for 1.0 Kb AM promoter; SEQ ID NO:4:
5'-TCT AGA ACT AGT TTT GTT AAT AAA TAA GTT GTA CAT-3'
Reverse primer AM-C for both AM promoters; SEQ ID NO:5:
5'-GAT TAA AAG CTT GTC TTG CTT TTA TTT TAT TTA GTA TTG-3'

Figure 6:
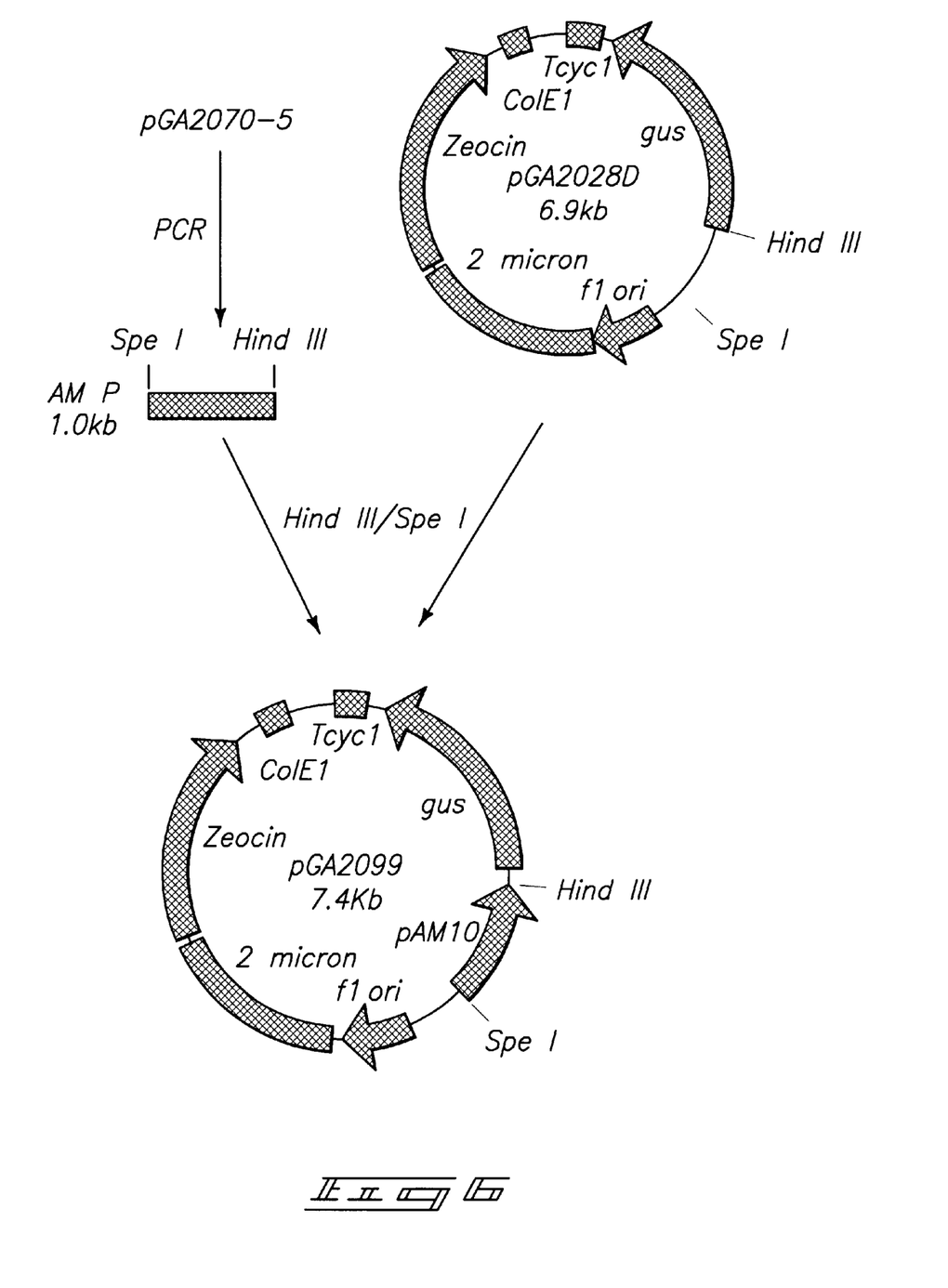
FIG. 6 is a schematic illustrating the construction of a plasmid vector pGA2099.

FIG. 5 shows the constructed vector pGA2098 containing the 1.55 kb AM promoter, and FIG. 6 shows the vector pGA2099 containing the 1.0 kb AM promoter, where 2 micron is a DNA replicon for plasmid replication in Saccharomyces strains; ColE1 is the origin for plasmid replication during gene manipulation in E. coli strains; f1 ori is the phage origin; gus is the bacterial glucuronidase gene; Tcyc1 is the transcription terminator; and Zeocin is the Zeocin resistance gene (Invitrogen, Inc, Carlsbad, Calif.). pAM15 and pAM10 stand for the AM promoter with lengths of 1.55 kb and 1.0 kb, respectively.

EXAMPLE 4

Glucuronidase (GUS) Expression Regulated by AM Promoter in Glucose Culture Medium.

A starch-degrading Saccharomyces hybrid yeast strain, obtained from James R. Mattoon of University of Colorado, was used as the host for plasmid transformation and promoter activity testing. A transformation kit (Invitrogen, Inc., Carlsbad, Calif.) was used for preparing competent yeast cells, which were subsequently used for the transformation of pGA2098 and pGA2099, respectively. After transformation, cells were plated onto YPD agar medium plate containing glucose 2%, yeast extract 1%, peptone 2%, and antibiotic Zeocin (Invitrogen, Inc., Carlsbad, Calif.). After four-day incubation at 30° C., transformed yeast colonies were obtained on the selective culture plate and used for the GUS activity analysis Colonies were picked, and intracellular protein samples were extracted using the glass-bead disintegrating method. Briefly, in this method, single transformed colony was suspended in 300 µl of extraction buffer containing 50 mM sodium phosphate at a pH 7.0, 1 mM EDTA, 1 mM phenylmethylsulfonyl fluoride (PMSF), 10 mM beta-mercaptoethanol, and 0.1% triton X-100. The cells were then disrupted by acid-washed glass beads (average diameter 100 µm) on a vortexer. After cell disruption, the sample was centrifuged at 20,000×g for 5 minutes. The supernatant was saved for both protein and GUS activity assays. Protein was determined using a BioRad protein assay reagent (Bio-Rad Laboratories, Hercules, Calif.) and glucuronidase activity using an enzymatic reaction in which a substrate 4-methylumbelliferul-beta-D-glucuronide (MUG) can be hydrolyzed by glucuronidase to a fluorescent compound 4-methylumbelliferone. One unit of glucuronidase activity is defined as the amount of glucuronidase that produces one pmole of 4-methyl umbelliferyl (MU) from MUG per minute at 37° C. The specific activity of glucuronidase is calculated as the units of glucuronidase per milligram of total protein.

After transformation, positive yeast colonies were selected and grown in YPD plates containing glucose as the main carbon source and an antibiotic, Zeocin. Transformed colonies were harvested, and protein samples were prepared. Table 2 shows the results of glucuronidase specific activities of both clones transformed with pGA2098 and pGA2099, respectively. Three transformants are under the control of the AM15 promoter, and four transformants are under the control of the AM10 promoter. It is evident that GUS activity is detected in all the tested clones, and the GUS activity is statistically above the non-transformed control cells, indicating that the isolated alpha-amylase promoter is active in the heterologous host, Saccharomyces sp. The GUS expression under AM10 promoter is higher than the one under the control of AM15 promoter.

TABLE 2

GUS activity in transformed Saccharomyces sp. colonies grown in medium containing glucose 2%, yeast extract 1%, and peptone 2%.

| Clone No. | Promoter | GUS specific activity (unit/mg) | Average activity (Unit/mg) |
|---|---|---|---|
| C* | — | 1.4 | 1.4 |
| 1 | AM15 | 2.5 | 2.3 ± 0.7 |
| 2 | | 1.7 | |
| 3 | | 2.8 | |
| 4 | AM10 | 4.8 | 4.5 ± 0.4 |
| 5 | | 3.9 | |
| 6 | | 4.8 | |
| 7 | | 4.6 | |

*Host cell without transformation of GUS expression vector.

EXAMPLE 5

Glucuronidase Expression Regulated by AM Promoter in Starch Culture Medium.

The GUS expression under alpha-amylase promoter exhibits lower activity, as shown in Table 2 when the culture medium contains glucose as the primary carbon source. In is test, transformed colonies were first grown in the medium containing glucose. After washing, cells were transferred into culture medium containing potato starch 2% yeast extract 1%, and peptone 2% for GUS the expression tests. Results are shown in Table 3. After a 15-hour growth period in the starch medium, intracellular protein samples were obtained using the glass-bead disintegrating method, and GUS activity was determined. GUS activity was detected in all transformed cultures. The highest GUS activity was 26 U/mg-protein under the control of the AM15 promoter, and 45 U/mg-protein under the control of AM10 promoter. The transformed GUS activity is above background level of the none-transformed cell sample. When induced by starch at its highest expression level, the transformed GUS activity is about 10-fold the activity in the glucose medium for both the AM15 promoter and the AM10 promoter. These results indicate that the alpha-amylase promoter is highly induced by starch, which can be used as an inexpensive inducting agent for gene expression regulation.

TABLE 3

GUS activity in transformed Saccharomyces sp. colonies grown in medium containing potato starch 2%, yeast extract 1%, and peptone 2%.

| Clone No. | Promoter | GUS specific activity (unit/mg) | Average activity (unit/mg) |
|---|---|---|---|
| C* | — | 7.7 | — |
| 1 | AM15 | 18.3 | 23.3 ± 2.9 |
| 2 | | 22.6 | |
| 3 | | 25.5 | |
| 4 | | 22.3 | |
| 5 | | 25.3 | |
| 6 | | 25.7 | |
| 7 | AM10 | 29.1 | 34.3 ± 6.4 |
| 8 | | 27.5 | |
| 9 | | 32.7 | |
| 10 | | 38.8 | |
| 11 | | 44.7 | |
| 12 | | 33.3 | |

*Host cell without transformation of GUS expression vector.

EXAMPLE 6

Glucuronidase Expression Regulated by Alpha-amylase Promoter in Plant Cells.

To test the functionality of alpha-amylase promoter in plant cell cultures, the plasmid vectors pGA2098 and pGA2099 were used in a transient plant cell protoplasting method. A 3-day old *Nicotiana tabacum* cell suspension was used for the preparation of protoplasts. Briefly, protoplasts were isolated by treating the suspension cells with a pH 5.8 solution containing 10 mg/l cellulase, 500 µg/ml pectoplyase (Kanematsu-Gosho, Los Angeles, Calif.) and 0.4 M D-mannitol at 28° C. for 20 minutes with a gentle shaking at 100 rpm. The protoplasts were then extensively washed with 0.4 M mannitol to remove cellulase and pectolyase. Finally, $1 \times 10^6$ protoplasts were resuspended in 0.5 ml of pH 5.5 electroporation buffer containing 2.38 mg/ml HEPES, 8.76 mg ml NaCl, 735 µg/ml CaCl2 and 0.4 M D-mannitol.

After addition of 20 µg superecoil plasmid DNA of pGA2098 and pGA2099, respectively, and 10 µg salmon sperm DNA as a carrier DNA, the protoplasts were them electroporated at a 300 volt pulse with 210 µF capacitor. The treated protoplasts were subsequently transferred in 7 ml of protoplast culture medium in a Petri dish and cultured for 48 hours at 28° C. The culture medium is a modified Murashige and Skoog (MS) medium (Murashige and Skoog, 1962) containing 4.3 mg/ml MS salt supplemented with 3% sucrose, 0.18 mg/ml $KH_2PO_4$, 0.1 mg/ml inositol, 1 µg/ml thiamine hydrochloride, and 0.2 µg/ml 2.4-dichlorophenoxyacetic acid (2.4-D), and 0.4 M D-mannitol.

The culture protoplasts were collected by gentle centrifugation and suspended in 100 µl extraction buffer containing 50 mM Tris-HCl pH 8.3, 227 mM NaCl, 1 mg/ml bovine serum albumin, and 1 mg/ml sodium azide. Protein samples were extracted by sonicating the protoplasts three times for 8 seconds with 30-second intervals. The protein samples were harvested by centrifuging the sonicated mixture at 15,000 g for 5 minutes. The supernatant was saved and protein concentration was measured by the Bio-Rad Protein Assay method (Bio-Rad, Hercules, Calif.). The glucuronidase activities were assayed using the same method as described in example 4. The glucuronidase activity results are shown in the following table. The results indicate that *S. castellii* alpha-amylase promoter can regulate the expression of glucuronidase in plant cells.

TABLE 4

GUS activity in electroporated *Nicotiana tabacum* cells.

| Test No. | Promoter | Culture Medium | GUS Specific Activity (unit/mg) |
| --- | --- | --- | --- |
| Control* | — | Sucrose | 2.6 |
| 1 | AM15 | Sucrose | 17.8 |
| 2 | | | 16.1 |
| 3 | | | 17.9 |
| 4 | | | 20.6 |
| 5 | AM10 | Sucrose | 26.5 |
| 6 | | | 14.4 |

*Host cell without transformation of glucuronidase expression vector.

We claim:

1. A method of expressing a gene product comprising:
   providing a host cell;
   introducing a DNA construct into the host cell, the construct comprising a nucleotide coding sequence that encodes a gene product operably linked to a promoter comprising at least nucleotides 1393 through 1961 of SEQ ID NO.:1; and
   expressing the gene product within the host cell.

2. The method of claim 1 wherein the host cell is a plant cell.

3. The method of claim 1 wherein the host cell is a plant protoplast.

4. The method of claim 1 wherein the host cell is a *Nicotinia tabacum* cell.

5. The method of claim 1 wherein the promoter comprises at least nucleotides 968 through 1961 of SEQ ID NO.:1.

6. The method of claim 1 wherein the gene product is an enzyme.

7. A host cell comprising a promoter operably linked to a coding sequence, the promoter comprising at least nucleotides 1393 through 1961 of SEQ ID NO.:6.

8. The host cell of claim 7 wherein the host cell is a plant cell.

* * * * *

UNITED STATES PATENT AND TRADEMARK OFFICE
CERTIFICATE OF CORRECTION

PATENT NO. : 6,551,798 B2
DATED : April 22, 2003
INVENTOR(S) : Gao et al.

It is certified that error appears in the above-identified patent and that said Letters Patent is hereby corrected as shown below:

Column 1,
Line 37, replace "Saccharomyces" with -- *Saccharomyces* --.

Column 2,
Line 2, replace "Schwanniomyces sp." with -- *Schwanniomyces sp.* --
Lines 5, 6, 23 and 28, replace "Schwanniomyces sp." with -- *Schwanniomyces sp.* --
Line 36, replace "*castellii*" with -- *castellii.* --.
Line 43, replace "Saccharomyces" with -- *Saccharomyces* --.

Column 3,
Line 11, replace "Schwanniomyces occidentalis" with -- *Schwanniomyces occidentalis* --.
Line 19, replace "GAMI" with -- GAM1 --.
Line 27, replace "alph-amylase" with -- alpha-amylase --.
Line 30, insert "." after "107".
Line 48, insert "." after "species".

Column 4,
Line 14, replace "Saccharomyces sp." with -- *Saccharomyces sp.* --.

Column 5,
Line 16, insert "." after "*castellii*".
Line 24, replace "GAT TCT AGA" with -- GAT *TCT AGA* --.
Line 27, replace "GAT GCA TGC" with -- GAT *GCA TGC* --.

Column 6,
Line 4, replace "CoE1" with -- ColE1 --.
Line 9, replace "those" with -- these --.
Line 16, replace "6" with -- 5 --.
Line 19, replace "OAT" with -- CAT --.
Line 32, replace "pGA202BD" with -- pGA2028D --.
Lines 41 and 45, replace "TCT AGA ACT AGT" with -- *TCT AGA ACT AGT* --.
Line 43, replace "Kb" with -- kb --.
Line 49, replace "GAT TAA AGA CTT" with -- *GAT TAA AGA CTT* --.
Lines 54 and 66, replace "Saccharomyces" with -- Saccharomyces --.
Line 57, replace "gus" with -- *gus* --.

UNITED STATES PATENT AND TRADEMARK OFFICE
CERTIFICATE OF CORRECTION

PATENT NO. : 6,551,798 B2
DATED : April 22, 2003
INVENTOR(S) : Gao et al.

It is certified that error appears in the above-identified patent and that said Letters Patent is hereby corrected as shown below:

Column 7,
Lines, 48 and 53, replace "Saccharomyces sp." with -- *Saccharomyces sp.* --.

Column 8,
Line 5, replace "is" with -- this --.
Line 8, insert "," after "2%".
Line 17, insert -- the -- after "above".
Line 18, replace "none" with -- non --.
Line 26, replace "Saccharomyces sp." with -- *Saccharomyces sp.* --.
Line 49, insert -- constructed -- after "the".
Line 50, insert -- assay using -- after "transient".
Line 64, replace "them" with -- then --.

Column 13,
Line 19, replace "1" with -- 6 --.

Column 14,
Line 15, replace "1" with -- 6 --.

Signed and Sealed this

Twenty-third Day of September, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 39
<212> TYPE: DNA
<213> ORGANISM: artificial sequence
<220> FEATURE:
<223> OTHER INFORMATION: oligonucleotide primer

<400> SEQUENCE: 1
gattctagaa acaactttac ttgtaaatcc ttcagttga                39

<210> SEQ ID NO 2
<211> LENGTH: 33
<212> TYPE: DNA
<213> ORGANISM: artificial sequence
<220> FEATURE:
<223> OTHER INFORMATION: oligonucleotide primer

<400> SEQUENCE: 2
gatgcatgca ccaatcgatt tatcaaatcg tta                      33

<210> SEQ ID NO 3
<211> LENGTH: 39
<212> TYPE: DNA
<213> ORGANISM: artificial sequence
<220> FEATURE:
<223> OTHER INFORMATION: oligonucleotide primer

<400> SEQUENCE: 3
tctagaacta gttatgataa atgaatattt tttattctt                39

<210> SEQ ID NO 4
<211> LENGTH: 36
<212> TYPE: DNA
<213> ORGANISM: artificial sequence
<220> FEATURE:
<223> OTHER INFORMATION: oligonucleotide primer

<400> SEQUENCE: 4
tctagaacta gttttgttaa taaataagtt gtacat                   36

```
<210> SEQ ID NO 5
<211> LENGTH: 39
<212> TYPE: DNA
<213> ORGANISM: artificial sequence
<220> FEATURE:
<223> OTHER INFORMATION: oligonucleotide primer

<400> SEQUENCE: 5
gattaaaagc ttgtcttgct tttatttat ttagtattg                              39

<210> SEQ ID NO 6
<211> LENGTH: 2000
<212> TYPE: DNA
<213> ORGANISM: Schwanniomyces castellii

<400> SEQUENCE: 6
agatcttcaa ataataatag atcctatgtt gatataagat caactccacc attgaccaat        60
tcatttaatc agcctcaaca acctcagcaa tcaatcaccg attctcctac ccctcaacat       120
catcaccaac attttttcc aacgcaatca attccttcca attctcaacc atccaccccg       180
ttggcttcaa atgatatcaa ttcaagattt caaccatttg gtcaacatac ccatttagct       240
ggtagtttta cgtcattaca gcaatcaacc tcaacttcgc aattagatga ttttagtaat       300
cctacttcaa caggtacgaa tgttaatgac tcaataagta ataaatttaa ttcattaaat       360
ttatcaaata ataattatga taattcctca ggaatttggg gtttaaaata acaaaccttt       420
ttgaaactcc aacattcaac tctttaatgt aatttatgat tatgataaat gaatatttt        480 tattcttttt gaataaaaat ttcgaataaa atattaataa gatgacaaaa aatgaataca       540
tgaatataca tatactttat ttaaaaaatt aatccttttg attaattgat gattttgctc       600
ttccaaaaag aaagaatccc agaaaataac aagttttcca aagggattaa caaaattttt       660
ttcctatttt tttatctttt tatcataata tagttctagt tcaatacgtt ttccaaaaat       720
gcaaaagtga aaaaatttt aaaaaaacat ttcgaaatta caaaaaaaag ttcattaaat       780
attattttat tttatcctat attatttcta acgatcttg aacaagtaac gttgttatta       840 ctacccgaa ggagaaaaag aaaatgattc ataacatgaa gtaatgctca cttaaaataa       900
cactgttaat acttttttaa tatatattaa tgtgcctcta atagattata tattattgtt       960 tgttttttt gttaataaat aagttgtaca tccatatttg tggttaaaac tttgaaaaaa      1020
ttattgttgt gacgacgtca cttggatctt atgaaagttt atttcaacct cactacatac      1080 aattttttc agctgaacca aattgttcac caatccaaat catatcagtt ctttctccct      1140
attatcaaag tcaaattgtc tctgcgtaca tattttcaat tatttaaacc ttaattaacc      1200
ttaaaaatat ctacctccct gagactctac gagggatag ttagttcttc ggaaatggta      1260
cgtggcgcta cctacccttc ccagtaactg tttcatcctg taatagaaac cgcttaactt      1320
gaatatttta tattacgtca taatacagaa ctattattat gtgattacaa tggtcggatt      1380
tttcttgttg atatgtgttc gtgggtggta cctgagctaa atttagaacc ggctatagat      1440
ccgcttgtct aaagaagaga taatgaagaa acaattaac cgagcactct tattaagttt      1500
ttttctattt tcttttgctc ctacttcaat aatttatcta aattgtattg tgcgttagat      1560
cagaatgtac tgataacaga gagtattatc atacacttgt ggatttcaaa aggcggaatc      1620
aaaagcatac gtagtcaaac ccttggttat ttgatgcaat taaggttgta gtcgttctta      1680
ccgatccatc attatacccc acacggttc atggtatgta ggtgtttcaa tagtgaagta      1740
caatgaatgt tttggtaatg ctgttattgt tggatcagta attatgttta aacaattaag      1800
```

-continued

```
ttctggaaaa tttattaaaa ttttacctac aattaagccg aaatccaatc gaaggtgccg    1860
cccagctggt gtataaatta ctcttgaaat tcaagttgaa cgtcgatact ctctaaagca    1920
aagctgttat tctacaatac taaataaaat aaaagcaaga catgagattt tcaactgaag    1980
gatttacaag taaagttgtt                                                2000
```